United States Patent
Hirata et al.

(10) Patent No.: US 7,660,676 B2
(45) Date of Patent: Feb. 9, 2010

(54) NUCLEIC ACID BASE SEQUENCE DETERMINING METHOD AND INSPECTING SYSTEM

(75) Inventors: Satoshi Hirata, Hachioji (JP); Satoshi Mitsuyama, Tokyo (JP); Hitoshi Matsuo, Musashino (JP); Shinichi Fukuzono, Hitachinaka (JP); Hiroyuki Suzuki, Hitachinaka (KP)

(73) Assignee: Hitachi, Ltd., Tokyo (JP)

( * ) Notice: Subject to any disclaimer, the term of this patent is extended or adjusted under 35 U.S.C. 154(b) by 367 days.

(21) Appl. No.: 10/315,143

(22) Filed: Dec. 10, 2002

(65) Prior Publication Data

US 2004/0110137 A1 Jun. 10, 2004

(51) Int. Cl.
*G06F 19/00* (2006.01)
(52) U.S. Cl. .......................................... 702/20; 702/19
(58) Field of Classification Search .................... 702/19, 702/20
See application file for complete search history.

(56) References Cited

FOREIGN PATENT DOCUMENTS

| JP | 4-294257 | | 3/1991 |
|---|---|---|---|
| JP | 05-322771 | * | 7/1993 |
| WO | WO 99/57547 | | 4/1999 |

OTHER PUBLICATIONS

Ewing et al. (Genome Research (1998) vol. 8, pp. 175-185; p. 176, col. 2 to p. 177, col. 1).*
Inazuka et al. (Genome Methods (1997) vol. 7, pp. 1094-1103).*

* cited by examiner

*Primary Examiner*—Lori A Clow
(74) *Attorney, Agent, or Firm*—Stites & Harbison PLLC; Juan Carlos A. Marquez, Esq.

(57) ABSTRACT

When the nucleic-acid base sequence of A, C, G, and T (or U) is determined by interpreting fluorescent-light intensity waveform data acquired by measuring nucleic-acid fragments, it is desirable to determine, with a high-accuracy, the base sequence at a location at which the data interpretation is difficult. In order to accomplish this object, the data interpretation is performed by making reference to information acquired by performing the statistical processing to plural pieces of fluorescent-light intensity waveform data corresponding to already-known base sequences. This method allows the determination of the nucleic-acid base sequence at the above-described location.

8 Claims, 8 Drawing Sheets

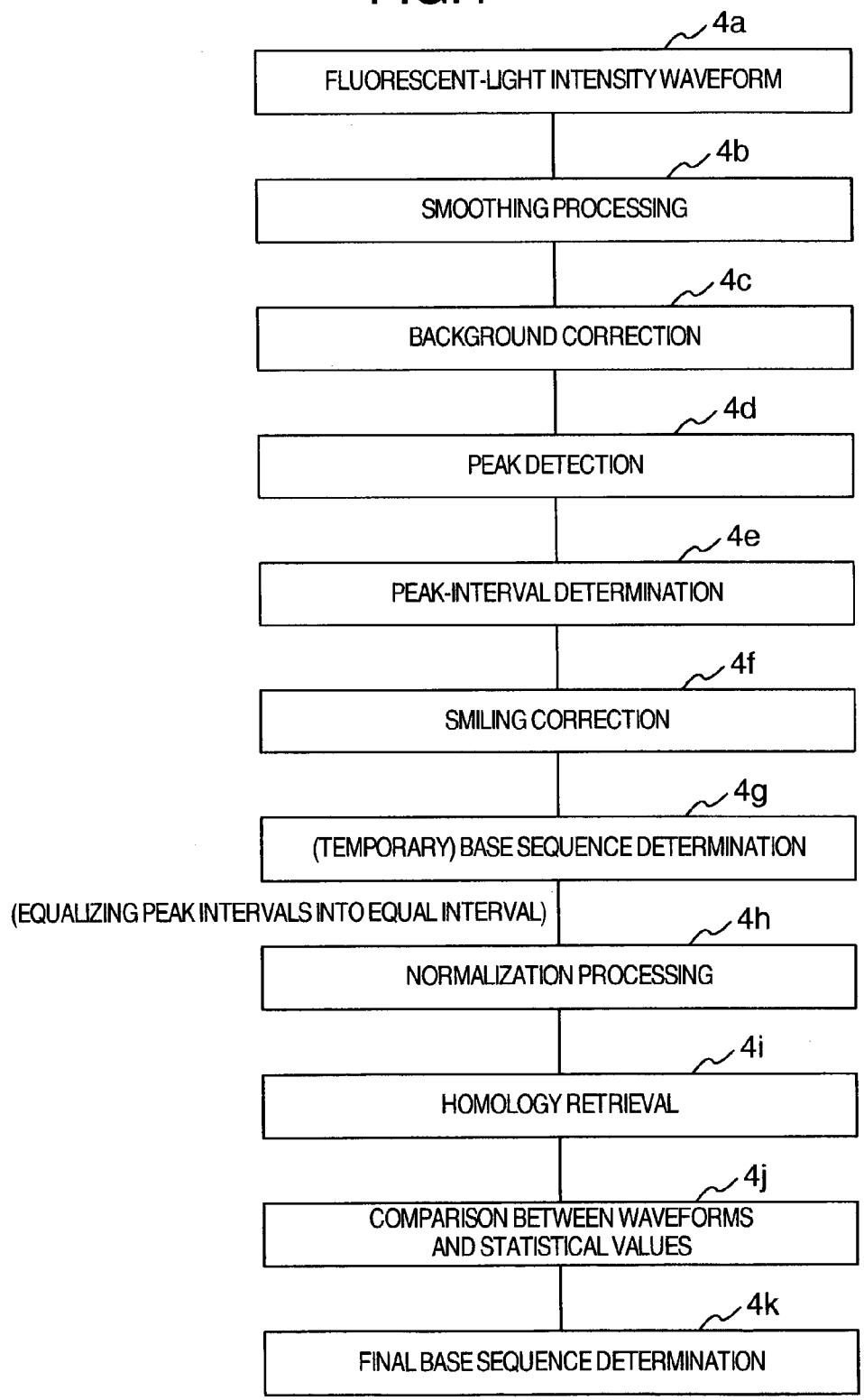

SEQUENCE LISTING

<160> NUMBER OF SEQ ID NOS: 7

<210> SEQ ID NO 1
<211> LENGTH: 10
<212> TYPE: DNA
<213> ORGANISM: Artificial Sequence
<220> FEATURE:
<221> NAME/KEY: misc_feature
<222> LOCATION: 7
<223> OTHER INFORMATION: v is a or c or g; chemically synthesized

<400> SEQUENCE: 1 aacgttvgac                                                            10

<210> SEQ ID NO 2
<211> LENGTH: 10
<212> TYPE: DNA
<213> ORGANISM: Artificial Sequence
<220> FEATURE:
<221> NAME/KEY: misc_feature
<222> LOCATION: 7
<223> OTHER INFORMATION: m is a or c; chemically synthesized

<400> SEQUENCE: 2 aacgttmgac                                                            10

<210> SEQ ID NO 3
<211> LENGTH: 10
<212> TYPE: DNA
<213> ORGANISM: Artificial Sequence
<220> FEATURE:
<221> NAME/KEY: misc_feature
<222> LOCATION: 7
<223> OTHER INFORMATION: m is a or c; chemically synthesized

<400> SEQUENCE: 3 aacgttmgac                                                            10

<210> SEQ ID NO 4
<211> LENGTH: 10
<212> TYPE: DNA
<213> ORGANISM: Artificial Sequence
<220> FEATURE:
<223> OTHER INFORMATION: chemically synthesized

<400> SEQUENCE: 4
aacgttcgac                                                            10

<210> SEQ ID NO 5
<211> LENGTH: 10
<212> TYPE: DNA
<213> ORGANISM: Artificial Sequence
<220> FEATURE:
<223> OTHER INFORMATION: chemically synthesized

<400> SEQUENCE: 5
aacgttagac                                                            10

<210> SEQ ID NO 6
<211> LENGTH: 10
<212> TYPE: DNA
<213> ORGANISM: Artificial Sequence
<220> FEATURE:
<221> NAME/KEY: misc_feature
<222> LOCATION: 7
<223> OTHER INFORMATION: m is a or c; chemically synthesized -continued

```
<400> SEQUENCE: 6 aacgttmgac                                                              10

<210> SEQ ID NO 7
<211> LENGTH: 10
<212> TYPE: DNA
<213> ORGANISM: Artificial Sequence
<220> FEATURE:
<221> NAME/KEY: misc_feature
<222> LOCATION: 7
<223> OTHER INFORMATION: v is a or c or g; chemically synthesized

<400> SEQUENCE: 7 aacgttvgac                                                              10
```

NUCLEIC ACID BASE SEQUENCE DETERMINING METHOD AND INSPECTING SYSTEM

BACKGROUND OF THE INVENTION

1. Field of the Invention

The present invention relates to a nucleic-acid base sequence determining method and an inspecting system therefor for determining the nucleic-acid base sequence by interpreting fluorescent-light intensity waveform data obtained from a nucleic-acid sample.

2. Description of the Related Art

In recent years, research for deciphering the human genetic information (i.e., human genome) has been enthusiastically carried out all over the world. In accompaniment therewith, it is now being clarified that the various diseases of humans are caused by mutations in the nucleic-acid (i.e., DNA) base sequence. Among individual humans, as is the case with their physical characteristics, the nucleic-acid base sequences differ from each other in many of the locations thereof. These differences in the base sequences are referred to as "polymorphisms". A polymorphism is defined as a base sequence in which certain base mutations exist with a frequency that is larger than 1% of the population. Examples of the polymorphisms are as follows: Polymorphisms where 1-base has been replaced by another base (i.e., Single Nucleotide Polymorphisms: SNPs), polymorphisms where 1-base to several tens of bases have been deleted or inserted, and polymorphisms where the repetition number of a location in which a 2-base to several-tens-of-base genetic base sequence is repeated differs from each other among individual humans.

It has been estimated that, within the 3-billion bases of the human genome, the mutations exist in a proportion of about 1 mutation every 500 to 1000 bases. Accordingly, 3-million or more 1-base mutation pairs (i.e., the SNPs) are considered to exist. The gene diagnosis method (i.e., the DNA marker method) where the SNPs like this or the like are employed as the marker is expected to be utilized for the search-for of disease genes, the judgement on disease sensitivities, and the development of proper medicines (i.e., the tailor-made therapy).

A lot of methods for detecting the polymorphisms like this at a low-cost and with ease have been developed up to the present. In whatever methods, however, a comparison is made between the sizes of nucleic-acid fragments thereby to recognize the mutations indirectly. Consequently, there are many cases where, as the final confirmation, a high-reliability base sequence determination is performed which allows the direct detection of the mutation locations. Conventionally, in order to perform this base sequence determination, there has been widely used the DNA sequencing method that results from combining the fluorescent-light labeling technique to the nucleic-acid fragments, the high-sensitivity fluorescent-light detecting technique, and the high-resolution gel electrophoresis technique.

In the above-described DNA sequencing method, at first, there is prepared a DNA whose base sequence is wished to be recognized (i.e., template DNA). Usually, the following nucleic-acid fragment is employed as the template DNA: A nucleic-acid fragment formed by incorporating a DNA whose base sequence is unknown into the plasmid (i.e., the DNA existing in the cytoplasm other than the nucleus within a cell of a bacteria or the like, and mainly having only replication staffing information), or a nucleic-acid fragment whose base sequence has been directly amplified by the polymerase chain reaction (: PCR) method. Next, the template DNA and a primer DNA (i.e., an oligonucleotide whose base sequence is complementary to the base sequence in a specific portion of the template DNA, and which corresponds to an oligonucleotide utilized as a one-side substance of the reaction when the PCR method is used) are mixed up in a solution inside a test tube. Moreover, the temperature is controlled so that the primer and the template will form a complementary double strand via hybridization (i.e., annealing).

Furthermore, the sequencing method proceeds to a step of replicating the DNA with this primer employed as a starting point. This replication is performed using the enzyme called "DNA polymerase" as the catalyst. The following 2 types of substances are poured into this reaction solution in a predetermined proportion, then mixed up in a predetermined concentration accordingly: dNTPs (: deoxy nucleotide triphosphates) needed for the synthesis of the DNA, i.e., monomers of the respective types of bases: adenine (A), cytosine (C), guanine (G), and thymine (T) (or, uracil (U)), and 4 types of ddNTPs (: dideoxy nucleotide triphosphates), i.e., terminators of A, C, G, and T (or U). While the DNA is being synthesized, this mixture with the ddNTPs permits the ddNTPs to be absorbed into the DNA synthesis, thereby preventing the DNA synthesis from proceeding any further.

As a result of this, nucleic-acid fragments are produced which have a ddNTP at their ends and whose syntheses have been stopped in various lengths (i.e., base lengths). Here, the ddNTPs are labeled in advance with fluorescent-light pigments whose colors differ depending on the respective bases. This, eventually, allows each nucleic-acid fragment to be labeled with a fluorescent-light color corresponding to the base positioned at its end. In addition, after having concentrated and refined the solution containing the nucleic-acid fragments produced in this way, the nucleic-acid fragments are denaturationized into single strands. Finally, the nucleic-acid fragments are separated on each base-length basis by using a gel electrophoresis apparatus.

Hereinafter, the explanation will be given below concerning the case where a capillary phoresis apparatus is used as one example of the above-described gel electrophoresis apparatus. At first, a capillary (i.e., glass narrow tube) is filled with a macromolecular polymer having a viscosity. Next, a voltage is applied to both ends of the capillary, thereby causing the nucleic-acid fragments having negative electric charges to be introduced and phoresied from one-side of the capillary.

Since the nucleic-acid fragments are chain-like polymerized macromolecules, the fragments move all over the polymer at speeds that are inversely proportional to the molecular weights. Namely, a shorter (i.e., smaller molecular weight) nucleic-acid fragment moves fast, while a longer (i.e., larger molecular weight) nucleic-acid fragment moves slowly. This condition makes it possible to separate the nucleic-acid fragments on each base-length basis. Moreover, the nucleic-acid fragments labeled with fluorescent-light pigments are irradiated with laser light at a position near the terminal end of the capillary (i.e., the position at which the respective nucleic-acid fragments become separable by the one base-length difference). Furthermore, a detector measures fluorescent-lights emitted from the respective bases fragments labeled with fluorescent-light pigments and positioned at the nucleic-acid fragments' ends. As described earlier, the fragments emit the fluorescent-lights in the order starting from the shortest nucleic-acid fragment. This condition makes it possible to obtain fluorescent-light intensity curves on the 4 base-type basis. Then, by comparing the 4 base-types of fluorescent-light intensities at each peak position or the like, it has become possible to perform the sequence determination of the base types (i.e., A, C, G, and T (U)).

FIG. 2 illustrates an example 2a of fluorescent-light intensity waveform data, and an example 2b of a base sequence (SEQ. ID No. 4) determined by interpreting this waveform data. In the drawing, the longitudinal axis denotes the fluorescent-light intensity, and the transverse axis denotes the phoresis time. Although, actually, the data equivalent to several hundreds of bases can be obtained at one measurement, only a part thereof has been illustrated here for explanation.

The heights of peaks appearing on the fluorescent-light intensity waveform data 2a reflect the quantity of a nucleic-acid fragment having a certain length. Usually, a longer nucleic-acid fragment is likely to exhibit its peaks at later phoresis times. Also, the peak intervals exhibit a tendency to become wider as the nucleic-acid fragment becomes longer. In view of this situation, there are some cases where a correction is made using a parameter determined by phoresis conditions such as the phoresis voltage so that the time axis of the display will be proportional to the base lengths.

In the nucleic-acid base sequence determining method according to the above-described prior art, there have frequently existed cases where there has been obtained a fluorescent-light intensity waveform from which it is difficult to determine the nucleic-acid base sequence. As the causes for these cases, the following factors can be considered: (a) the quantity of the nucleic-acid fragments is small, which makes the signal intensity weak, (b) the nucleic-acid fragments take the secondary structure by themselves, which generates an extra signal component, (c) the refinement degree of a nucleic-acid sample whose base sequence is to be determined is low, which produces a nucleic-acid fragment that generates an extra signal component, (d) the conditions at the time of a sequence reaction and the electrophoresis cause distortions to occur in the signal, or the like.

In many cases, these problems, in general, can be solved as follows: After having determined the base sequence of a nucleic acid whose base sequence is complementary to that of a nucleic-acid sample whose base sequence is to be determined, a comparison/checking is made between the mutually complementary 2 base sequences thus obtained. This method, however, requires the preparation of the 2 samples and the 2-times determinations of the respective base sequences, which necessitates 2-fold time and labor. What is more, there are some cases where, depending on the samples, it is impossible to obtain the data on the mutually complementary 2 base sequences.

When deciphering a completely unknown base sequence, the above-described problems frequently become the obstacles thereto. In the actual base sequence determination of a nucleic-acid sample, however, there are not a few cases where, just like the case of inspecting a mutation in a certain specific location of the base sequence, there has been already known at least a part of the base sequence of the nucleic-acid sample whose base sequence is to be determined. When, in this way, there exist the already-known base sequence like this to which reference can be made, the interpretation of the nucleic-acid fragment detection data is performed by making reference to the already-known base sequence by some method or other. Namely, there are prepared the already-known fluorescent-light intensity waveform and the already-known base sequence corresponding thereto (i.e., arrangements of the base-type characters: A, C, G, and T). Then, a comparison/checking is made with a newly-acquired fluorescent-light intensity waveform of the nucleic-acid fragments, thereby allowing the base sequence to be determined.

However, in the above-described comparison/reference between the newly-acquired fluorescent-light intensity waveform of the nucleic-acid fragments, the already-known fluorescent-light intensity waveform thereof and the already-known base sequence corresponding thereto, the comparison/reference needs to be made by visually checking. This has resulted not only in the problem of requiring time and labor to do the checking, but also in the problem of mutually different determinations being made by the respective judges if the comparison criterion is indefinite.

Moreover, if the conditions at the time of the sequence reaction and the electrophoresis have changed on each measurement basis causing different distortions to occur in the signal, there has existed the following problem: Based on only the one example of the fluorescent-light intensity waveforms between which the comparison/reference is to be made, making the judgement itself becomes difficult. Also, when simultaneously comparing/checking examples of a plurality of fluorescent-light intensity waveforms, the large number of waveforms are displayed in a limited space. This has resulted in the problem that the comparison itself becomes difficult or the problem that the redundancy of the comparison criterion increased.

SUMMARY OF THE INVENTION

In the present invention, in order to solve the above-described problems, in a nucleic-acid base sequence determining apparatus including a unit for formulating a nucleic-acid fragment originating from a nucleic-acid sample, a unit for separating the formulated nucleic-acid fragment on each base-length basis, and labeling the separated nucleic-acid fragments with .a fluorescent-light substance, a unit for electrophoresis of the fluorescent-light substance-labeled nucleic-acid fragments so as to detect fluorescent-light intensity waveform data, and a unit for determining the base sequence of the nucleic-acid fragment by interpreting the detected fluorescent-light intensity waveform data, wherein the base sequence determining unit has a function for storing information obtained by performing a statistical processing to plural pieces of fluorescent-light intensity waveform data corresponding to already-known base sequences, and a function for determining the base sequence by making a comparison between the information obtained by the statistical processing and the detected fluorescent-light intensity waveform data.

Also, in the present invention, in order to solve the above-described problems, in a nucleic-acid base sequence determining method including the steps of a calculation processing for calculating fluorescent-light intensity waveform data obtained by electrophoresis of various lengths of nucleic-acid fragments formulated from a nucleic-acid sample, and a storage processing for storing the calculation result obtained by the calculation processing, the calculation processing includes a step of calculating the signal intensities of the respective peaks in fluorescent-light intensity waveform data corresponding to already-known base sequences, the storage processing including a step of recording information on the signal intensities of the respective peaks.

Also, in the present invention, in order to solve the above-described problems, in a nucleic-acid base sequence determining method including the steps of a calculation processing for calculating fluorescent-light intensity waveform data obtained by electrophoresis of various lengths of nucleic-acid fragments formulated from a nucleic-acid sample, and a storage processing for storing the calculation result obtained by the calculation processing, the calculation processing includes a step of performing a statistical processing to plural pieces of fluorescent-light intensity waveform data corresponding to already-known base sequences, and calculating the statistical value of the respective peak intensities in the plural pieces of fluorescent-light intensity waveform data, the storage processing including a step of recording the statistical value of the respective peak intensities.

Also, in the present invention, in order to solve the above-described problems, in a nucleic-acid base sequence determining method including the steps of a calculation processing for calculating fluorescent-light intensity waveform data obtained by electrophoresis of various lengths of nucleic-acid fragments formulated from a nucleic-acid sample, and a storage processing for storing the calculation result obtained by the calculation processing, the calculation processing includes a step of calculating the mean value of the respective peak intensities in plural pieces of fluorescent-light intensity waveform data.

Also, in the present invention, in order to solve the above-described problems, in a nucleic-acid base sequence determining method including the steps of a calculation processing for calculating fluorescent-light intensity waveform data obtained by electrophoresis of various lengths of nucleic-acid fragments formulated from a nucleic-acid sample, and a storage processing for storing the calculation result obtained by the calculation processing, the calculation processing includes a step of calculating the maximum value and/or the minimum value of the respective peak intensities in plural pieces of fluorescent-light intensity waveform data.

Also, in the present invention, in order to solve the above-described problems, in a nucleic-acid base sequence determining method including the steps of a calculation processing for calculating fluorescent-light intensity waveform data obtained by electrophoresis of various lengths of nucleic-acid fragments formulated from a nucleic-acid sample, and a storage processing for storing the calculation result obtained by the calculation processing, the calculation processing includes a step of performing a preprocessing for making the criterions of all the peak intensities identical to each other among all the fluorescent-light intensity waveform data.

Also, in the present invention, in order to solve the above-described problems, in a nucleic-acid base sequence inspecting system for interpreting fluorescent-light intensity waveform data obtained by electrophoresis of various lengths of nucleic-acid fragments formulated from a nucleic-acid sample, and thereby determining the base sequence of the nucleic-acid fragments, and displaying the determined base sequence information and the fluorescent-light intensity waveform, there are provided a function for recording information on the signal intensities of the respective peaks in fluorescent-light intensity waveform data corresponding to already-known base sequences, a function for determining the base sequence by making a comparison between the recorded information on the signal intensities of the respective peaks and the fluorescent-light intensity waveform data, and a function for displaying, by a box-and-whisker plot, the recorded information on the signal intensities of the respective peaks.

Also, in the present invention, in order to solve the above-described problems, in a nucleic-acid base sequence inspecting system for determining the base sequence of a nucleic-acid fragment by interpreting fluorescent-light intensity waveform data whose judgement request has been accepted from an inspection-requesting party, there are provided a function for recording information on the signal intensities of the respective peaks in fluorescent-light intensity waveform data corresponding to already-known base sequences, a function for determining the base sequence by making a comparison between the recorded information on the signal intensities of the respective peaks and the fluorescent-light intensity waveform data, and a function for reporting the determined base sequence to the inspection-requesting party.

Other objects, features and advantages of the invention will become apparent from the following description of the embodiments of the invention taken in conjunction with the accompanying drawings.

BRIEF DESCRIPTION OF THE DRAWINGS

FIG. 4 is a procedure-step diagram for explaining the procedure-step of the base sequence determination in the present invention;

DETAILED DESCRIPTION OF THE EMBODIMENTS

Figure 3:
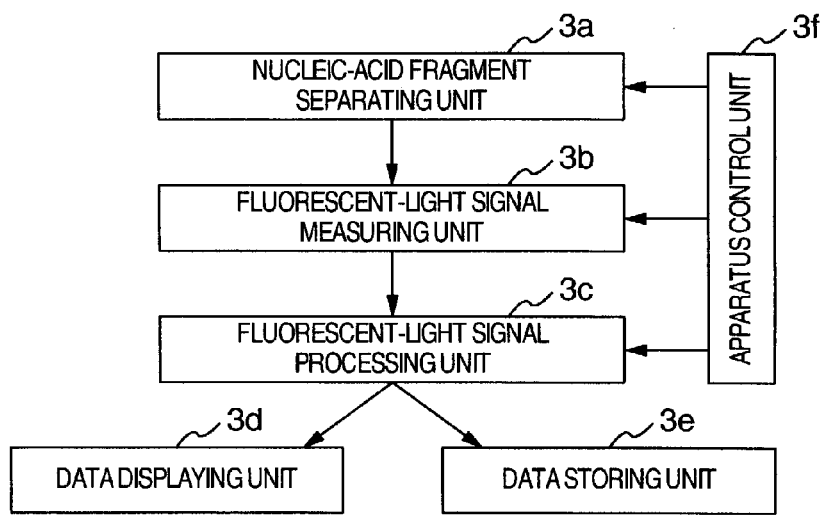
FIG. 3 is a block diagram for illustrating the configuration example of a nucleic-acid base sequence determining apparatus.

FIG. 3 illustrates the configuration example of a nucleic-acid base sequence determining apparatus to which the present invention is applied. This apparatus includes the following configuration components: A nucleic-acid fragment separating unit $3a$ for electrophoresis of fluorescent-light-labeled nucleic-acid fragments so as to separate the nucleic-acid fragments on the basis of differences in the base lengths, a fluorescent-light signal measuring unit $3b$ including components such as an optical appliance for irradiating the separated nucleic-acid fragments with laser light and a detector for detecting fluorescent-lights thus generated, a fluorescent-light signal processing unit $3c$ for performing a signal processing to the measured fluorescent-light intensity waveform data so as to determine the base sequence and the like, a data displaying unit $3d$ for displaying the fluorescent-light intensity waveform data, the determined base sequence, and the like, a data storing unit $3e$ for recording the fluorescent-light intensity waveform data, the determined base sequence, and the like, and an apparatus control unit $3f$ for controlling the above-described respective units.

Here, the control unit $3f$ performs the following controls: The power-supply control for the nucleic-acid fragment separating unit $3a$, the light-source control in the fluorescent-light signal measuring unit $3b$ and the sampling condition control for the detector, the data transfer control among the fluorescent-light signal processing unit $3c$, the data displaying unit 3d, and the data storing unit 3e, the control over the data processing contents in the fluorescent-light signal processing unit 3c, and the like.

In order to determine the base sequence by using the above-described apparatus in FIG. 3, as is the case with the method explained in the prior art, the following processing is performed at first: Namely, in the nucleic-acid fragment separating unit 3a, based on a nucleic-acid sample whose base sequence is to be determined, various lengths of nucleic-acid fragments are formulated using Sanger method or the like. In this reaction, the use of a primer or ddNTPs labeled with fluorescent-light pigments permits the nucleic-acid fragments to be labeled with the fluorescent-light pigments.

Next, in the fluorescent-light signal processing unit 3c, the following processings are performed with respect to the labeled nucleic-acid fragments, thereby performing the determination of the base sequence: Namely, in the fluorescent-light signal processing unit 3c, as illustrated in FIG. 4, a smoothing processing 4b, a background correction 4c, a peak detection 4d, and a peak-interval determination 4e are usually performed with respect to the fluorescent-light intensity waveform data 4a on the labeled nucleic-acid fragments. Also, the peak intervals do not always become equal to a constant value because of a phoresis non-uniformity (i.e., smiling) at the time of the electrophoresis. Accordingly, depending on the magnitudes of the peak intervals determined, corrections of the peak positions are performed as required (i.e., smiling correction 4f). Moreover, comparisons are made among the signal intensities of the respective base types at each peak position (or areas of the respective peaks or the like). These comparisons allow the base types to be sequentially determined in accordance with a predetermined identification criterion (i.e., (temporary) base sequence determination 4g).

Examples of this identification criterion are as follows: If the signal intensity of a certain base type (e.g., A) at a certain fixed peak position is the largest signal intensity, and if the signal intensity of a base type (e.g., C) whose signal intensity is the largest of the remaining 3 base types is less than T % (T is a threshold value, e.g., 50%) of the signal value of the largest base type (here, A), the base type is identified as the largest base type (here, A). Also, if the signal intensity of the second base type (here, C) is larger than T % (e.g., 50%) of the signal value of the largest base type (here, A), and if the signal intensity of the third base type (here, G) is less than T % (e.g., 50%) thereof, the base type is determined as a hetero (here, M: the IUB standard mixed-base representation scheme) of the largest base type (here, A) and the second base type (here, C). Although, in a similar way, the mixed-base representation schemes (i.e., the IUB standard mixed-base representation scheme) have been stipulated in correspondence with all the combinations, no definite criterion has been included in their judgement criterions.

In the above-described nucleic-acid base sequence determining method, as described earlier, there exist the cases where, because of the various causes described, there has been obtained the fluorescent-light intensity waveform based on which it is difficult to determine the nucleic-acid base sequence. In particular, when deciphering a completely unknown base sequence, the above-described cases frequently become the obstacles thereto. In the actual base sequence determination of a nucleic-acid sample, however, there are many cases where, just like the case of inspecting a mutation in a certain specific location of the base sequence, there has been already known at least a part of the base sequence of the nucleic-acid sample whose base sequence is to be determined. If there exist a plurality of already-known base sequences like this to which reference can be made, it is possible to cause the fluorescent-light signal processing unit 3c to execute the following function: Performing the interpretation of the nucleic-acid fragment detection data by making reference to information obtained by performing a statistical processing to plural pieces of fluorescent-light intensity waveform data corresponding to already-known base sequences.

Figure 5:
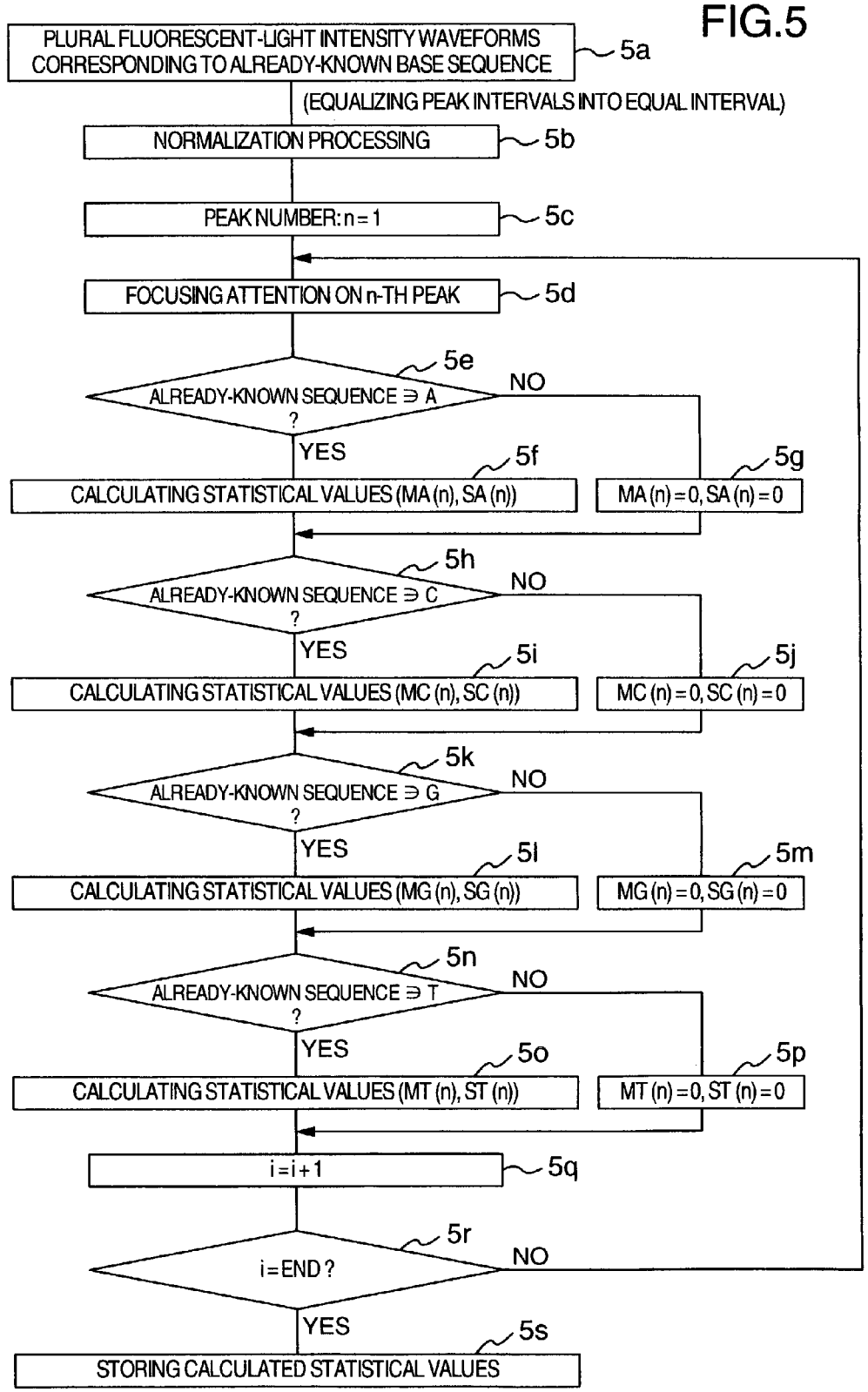
FIG. 5 is a procedure-step diagram for explaining a statistical processing to the fluorescent-light intensity waveform data according to the present invention.

Hereinafter, referring FIG. 5 and FIG. 1, the explanation will be given below concerning the concrete processing contents of the above-described statistical processing, and the processing contents for determining the base sequence of the newly-acquired data by using the statistical information thus obtained.

At first, there are prepared a plurality of fluorescent-light intensity waveform data sets where the base sequence in a specific range has been already known (the fluorescent-light intensity waveform data by the amount of the 4 base types is defined as the 1 set), and the identified base sequence in each data set (5a). Incidentally, when obtaining the plural pieces of fluorescent-light intensity waveform data corresponding to already-known base sequences, there is used a method such as the above-described method for determining the base sequences of the 2 nucleic acids whose base sequences are mutually complementary.

Next, with respect to each fluorescent-light intensity waveform data set, a normalization processing 5b is performed at all the peak positions by the signal intensity of a base type that has a maximum fluorescent-light intensity. For example, letting the fluorescent-light intensities of the 4 base types at a certain peak position (e.g., the peak number n) be $A_0(n)$, $C_0(n)$, $G_0(n)$, and $T_0(n)$ (or $U_0(n)$), respectively, $A(n)$, $C(n)$, $G(n)$, and $T(n)$ (or $U(n)$), i.e., the values of the fluorescent-light intensities after the normalization processing, are calculated by the following equations (1) to (4), respectively:

$$A(n)=A_0(n)/\max\{A_0(n),C_0(n),G_0(n),T_0(n)(\text{or } U_0(n))\} \quad (1)$$

$$C(n)=C_0(n)/\max\{A_0(n),C_0(n),G_0(n),T_0(n)(\text{or } U_0(n))\} \quad (2)$$

$$G(n)=G_0(n)/\max\{A_0(n),C_0(n),G_0(n),T_0(n)(\text{or } U_0(n))\} \quad (3)$$

$$T(n)(\text{or } U(n))=T_0(n)(\text{or } U_0(n))/\max\{A_0(n),C_0(n),G_0(n),T_0(n)(\text{or } U_0(n))\} \quad (4)$$

Here, max $\{A_0(n), C_0(n), G_0(n), T_0(n)$ (or $U_0(n))\}$ indicates a function that, of $A_0(n)$, $C_0(n)$, $G_0(n)$, and $T_0(n)$ (or $U_0(n)$), takes the maximum value. Incidentally, in addition to the signal values at the peak position, all the signal values before and after the peak positions at which the peaks are formed are normalized by the above-described max $\{A_0(n), C_0(n), G_0(n), T_0(n)$ (or $U_0(n))\}$. This makes it possible to perform the normalization of the entire peaks as well. Also, as the denominator employed when performing the normalization, the maximum peak area may be employed instead of the above-described maximum peak intensity. Also, if the peak positions differ little by little for each data set of different samples, before performing the normalization processing, an interpolation data processing, a thin-out data processing, or the like for equalizing all the peak intervals into an equal interval may also be performed so that the peak positions of the respective fluorescent-light intensity waveforms will coincide with each other among the data sets.

Next, with respect to the plurality of fluorescent-light intensity waveform data sets after the normalization processing, the mean value M and the standard deviation S of the signal values at each peak position (or each sampling position) are calculated on each identified base basis. Here, it has been already recognized that, at a certain peak position (e.g., the peak number n), the base types at the peak position include at least the base type A (i.e., any one case of A alone, a homo of A, and a hetero of A with another base type). At this time, for example, if the fluorescent-light intensity waveform data on A exists by the amount of m samples (i.e., A1(n), A2(n), . . . , Am(n)) (5c to 5e), the mean value MA(n) and the standard deviation SA(n) of the fluorescent-light intensities of the base type A at the peak number n are calculated by the following equation (5) and equation (6), respectively (5f):

$$MA(n) = \sum_{i=1}^{m} Ai(n)/m \quad (5)$$

$$SA(n) = \sqrt{\sum_{i=1}^{m}\{Ai(n)\}^2/m - \left\{\sum_{i=1}^{m} Ai(n)/m\right\}^2} \quad (6)$$

Similarly, with respect to the remaining base types C, G, and T (or U), concerning the fluorescent-light intensity waveform data on each base type where it has been already recognized that the base types at a certain peak position (e.g., the peak number n) include at least each base type, the mean values MC(n), MG(n), and MT(n) (or MU(n)), and the standard deviations SC(n), SG(n), and ST(n) (or SU(n)) are calculated (5h to 5i, 5k to 5l, and 5n to 5o).

However, at a certain peak position (e.g., the peak number n), when there exists only 1 type of already-known base type (i.e., when there exists no already-known polymorphism), when there exist 2 types of polymorphisms, and when there have been known 3 types of polymorphisms, it is advisable to perform the above-described calculations of the mean value and the standard deviation concerning only the already-known base type or types respectively. Incidentally, when there exists none of the waveform data on the already-known base types, it is allowable to substitute 0 or the like into the mean value and the standard deviation in order to indicate that there exists no already-known base type data (5g, 5j, 5m, and 5p). Otherwise, in all the data sets identified as another base type, it is also allowable to calculate and substitute the mean value and the standard deviation of the fluorescent-light intensities of the base type.

As is the case with the above-described series of procedure-steps, the mean values and the standard deviations at all the peak positions are sequentially calculated, then recording the calculation results into the data storing unit 3e (5q to 5s).

Next, the explanation will be given below concerning a method for performing the base sequence determination of the newly-acquired fluorescent-light intensity waveforms by using the mean values and the standard deviations obtained in this way.

Figure 1:
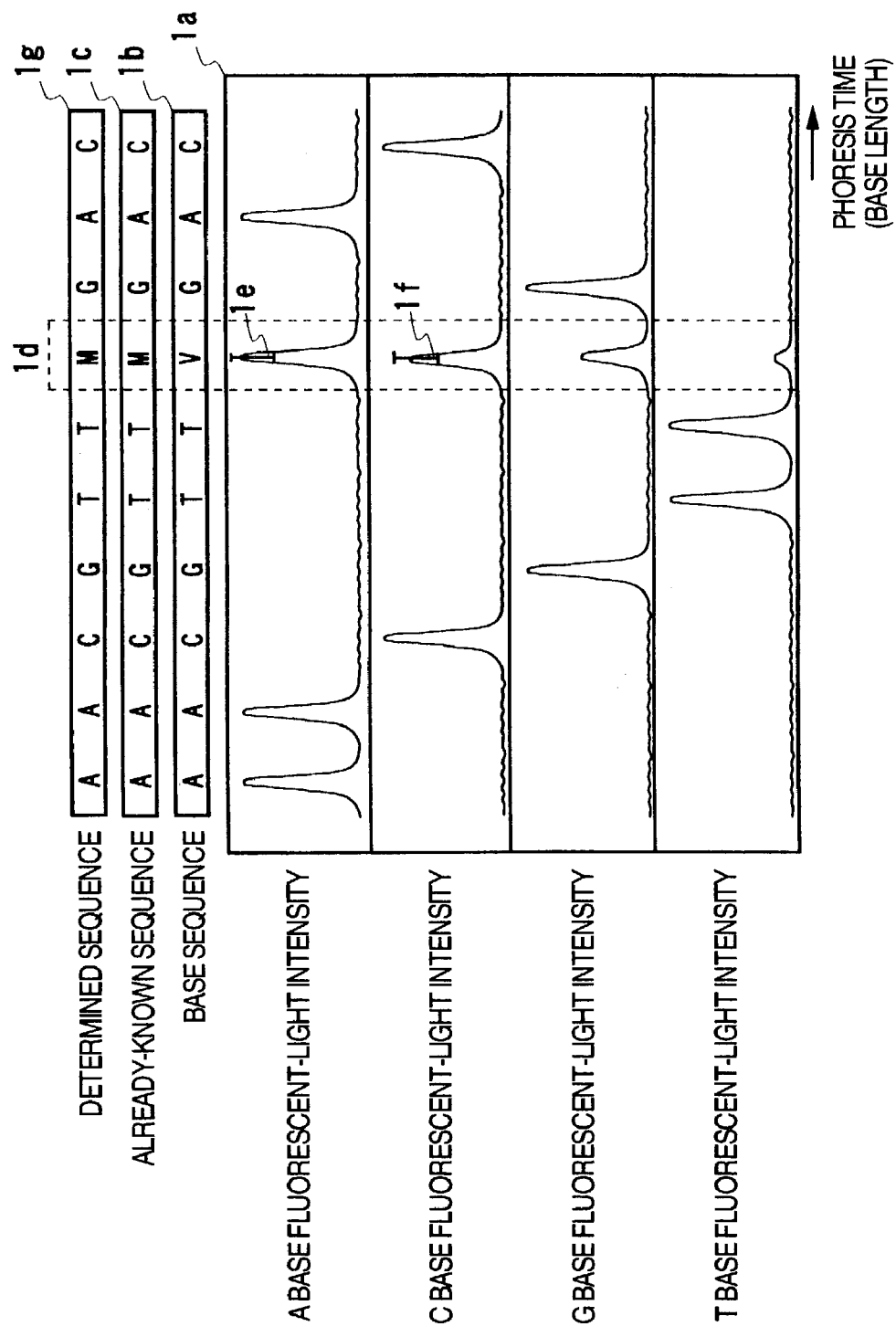
FIG. 1 is an explanatory diagram for explaining the base sequence determination using box-and-whisker plots according to the present invention.
Figure 2:
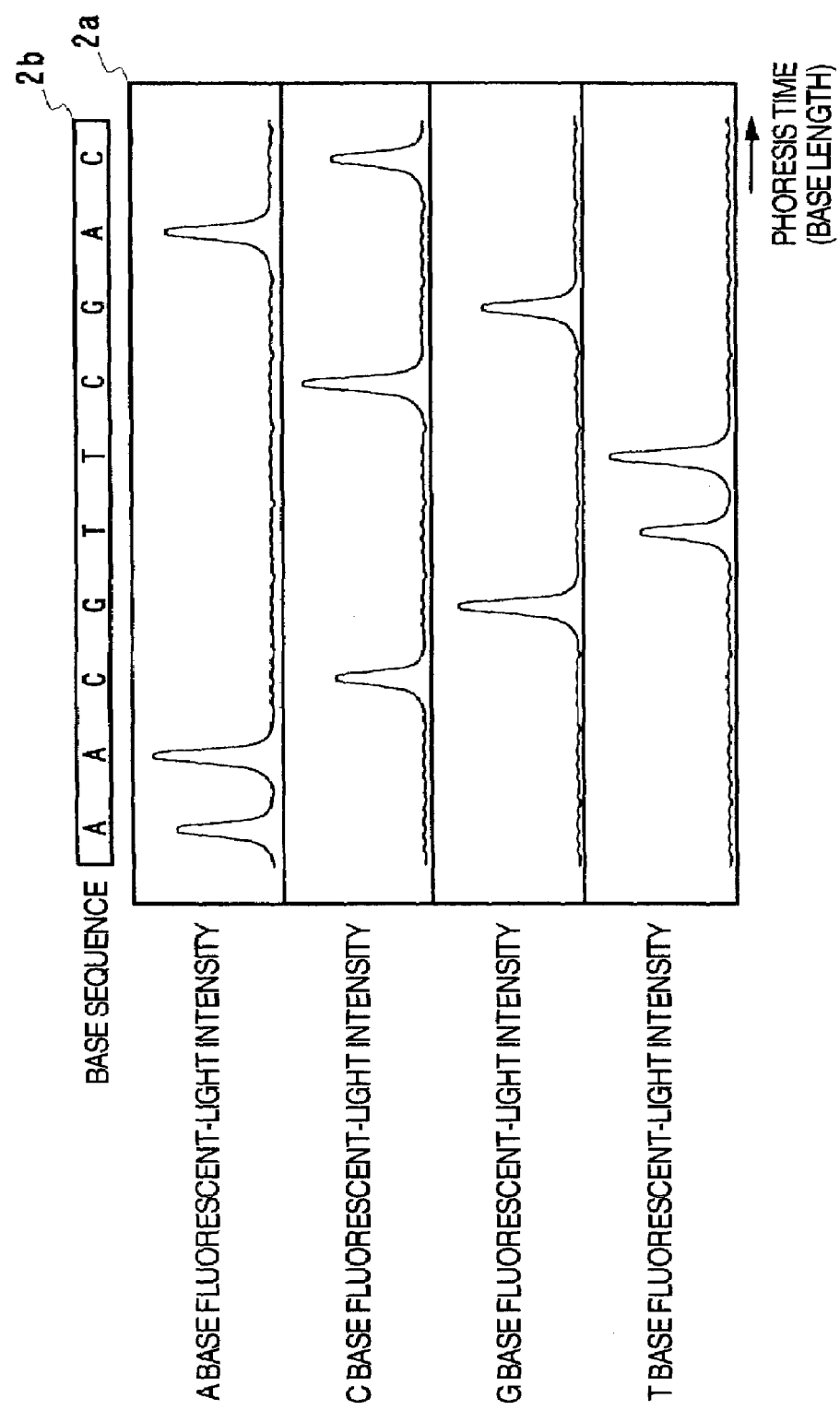
FIG. 2 is the explanatory diagram for illustrating the example of the fluorescent-light intensity waveform data and that of the base sequence in the conventional method.

FIG. 1 illustrates the following data: The after-the normalization processing (4h in FIG. 4) fluorescent-light intensity waveform data 1a (whose entire peaks have been normalized) including a location (1d) at which determining the base sequence is difficult, the temporarily-determined base sequence 1b (SEQ. ID No. 1) determined temporarily (4g) by the above-described conventional identification criterion (e.g., the threshold value=50%), a base sequence portion 1c (SEQ. ID No. 2) that exhibits a high homology (i.e., mutually-homologous property) with the already-known base sequence as a result of being obtained by performing a homology retrieval (4i) of the base sequence 1b with respect to the already-known base sequence, and, by box-and-whisker plots 1e and 1f (see FIG. 6), the mean values and the standard deviations calculated from the plural pieces of fluorescent-light intensity waveform data identified as the base sequence 1c. Additionally, the operation of the above-described homology retrieval may be performed as follows: The already-known base sequence data are shifted on one-base basis with respect to the base sequence 1b on the display screen by a manual operation. Otherwise, the operation may be automatically performed utilizing a homology-analyzing algorithm that has been generally known already.

Figure 6:
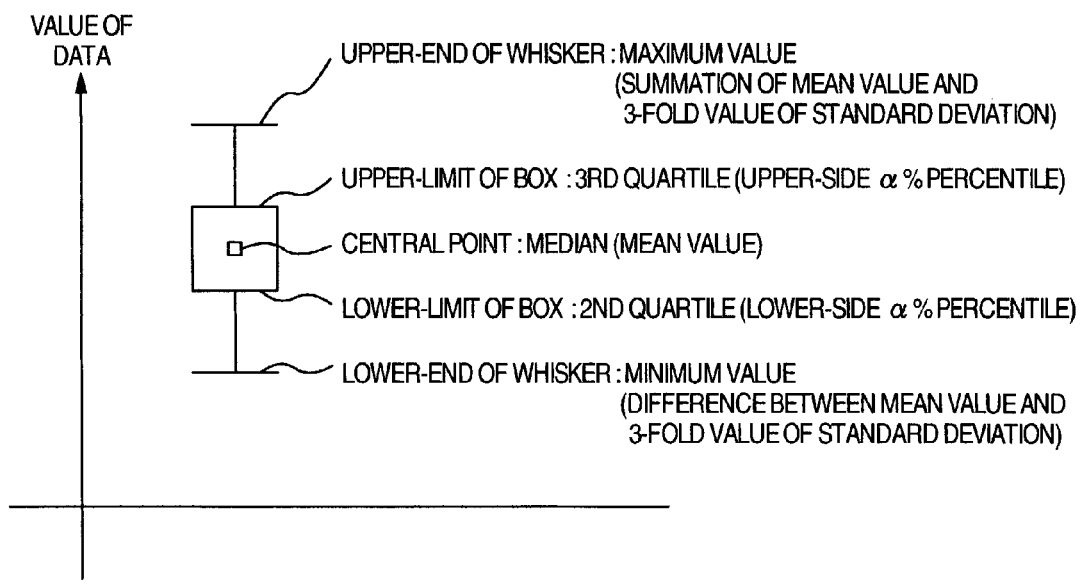
FIG. 6 is an explanatory diagram for explaining the box-and-whisker plots.

In the box-and-whisker plots in FIG. 6, the summation of a mean value and the 3-fold value of a standard deviation (e.g., MA(n)+3×SA(n)) is defined as the upper-limit value, and the difference between the mean value and the 3-fold value of the standard deviation (e.g., MA(n)−3×SA(n)) is defined as the lower-limit value. At the location 1d in FIG. 1, the box-and-whisker plots are displayed on the waveform of the base A and that of the base C. This indicates that, at the location 1d, there exist the already-known data identified as the base type A and the already-known data identified as the base type C. Here, with respect to the base G and the base T (or U), since there exists none of the identified already-known data, i.e., the mean values and the standard deviations are equal to 0, no box-and-whisker plots are displayed thereon.

Moreover, as illustrated in FIG. 1, at the location 1d in the newly-acquired fluorescent-light intensity waveforms 1a, the signal quantity of the fluorescent-light indicating the base type A is positioned between the upper-limit value and the lower-limit value indicated in the box-and-whisker plot 1e, and the signal quantity of the fluorescent-light indicating the base type C is positioned between the upper-limit value and the lower-limit value indicated in the box-and-whisker plot 1f (4j). This condition allows this unknown base type to be identified as a hetero (i.e., M in the IUB standard mixed-base representation scheme) of A and C, thereby making it possible to acquire a determined sequence 1g (4k)(SEO. ID No. 3).

Additionally, when identifying the base type, the above-described fluorescent-light signal processing unit 3c may execute a function for automatically determine the base type in accordance with the above-described judgement condition of "the fluorescent-light signal quantity is positioned between the upper-limit value and the lower-limit value". Otherwise, it is also allowable to provide the fluorescent-light signal processing unit 3c with a function for permitting the operator to rewrite the base type from V to M by a manual operation.

Then, after having sequentially identified the unknown base types similarly, the determined base sequence is recorded into the data storing unit 3e. In this way, the determination of the nucleic-acid base sequence is performed using the nucleic-acid base sequence determining apparatus having the above-described series of functions. This makes it possible to acquire a high determination-accuracy base sequence.

Incidentally, in the above-described embodiment, the explanation has been given concerning the case where, if the fluorescent-light signal quantity of a certain base type is positioned between the upper-limit value and the lower-limit value in the box-and-whisker plot, the unknown base type is automatically identified as this base type. Even if, however, the fluorescent-light signal quantity exceeds the upper-limit value in the box-and-whisker plot, the unknown base type may also be identified as this base type.

Also, in the above-described embodiment, the explanation has been given regarding the following case: In the temporarily-determined base sequence determined temporarily by using the conventional identification criterion, with respect to only the location at which it is difficult to determine the base sequence by using the conventional identification criterion, determining the base sequence has been performed by making reference to the above-described statistically-processed result. Moreover, at all the locations subsequent to the primer whose base sequence has been already known, making reference to the statistically-processed result makes it possible to determine the base sequence.

Figure 7:
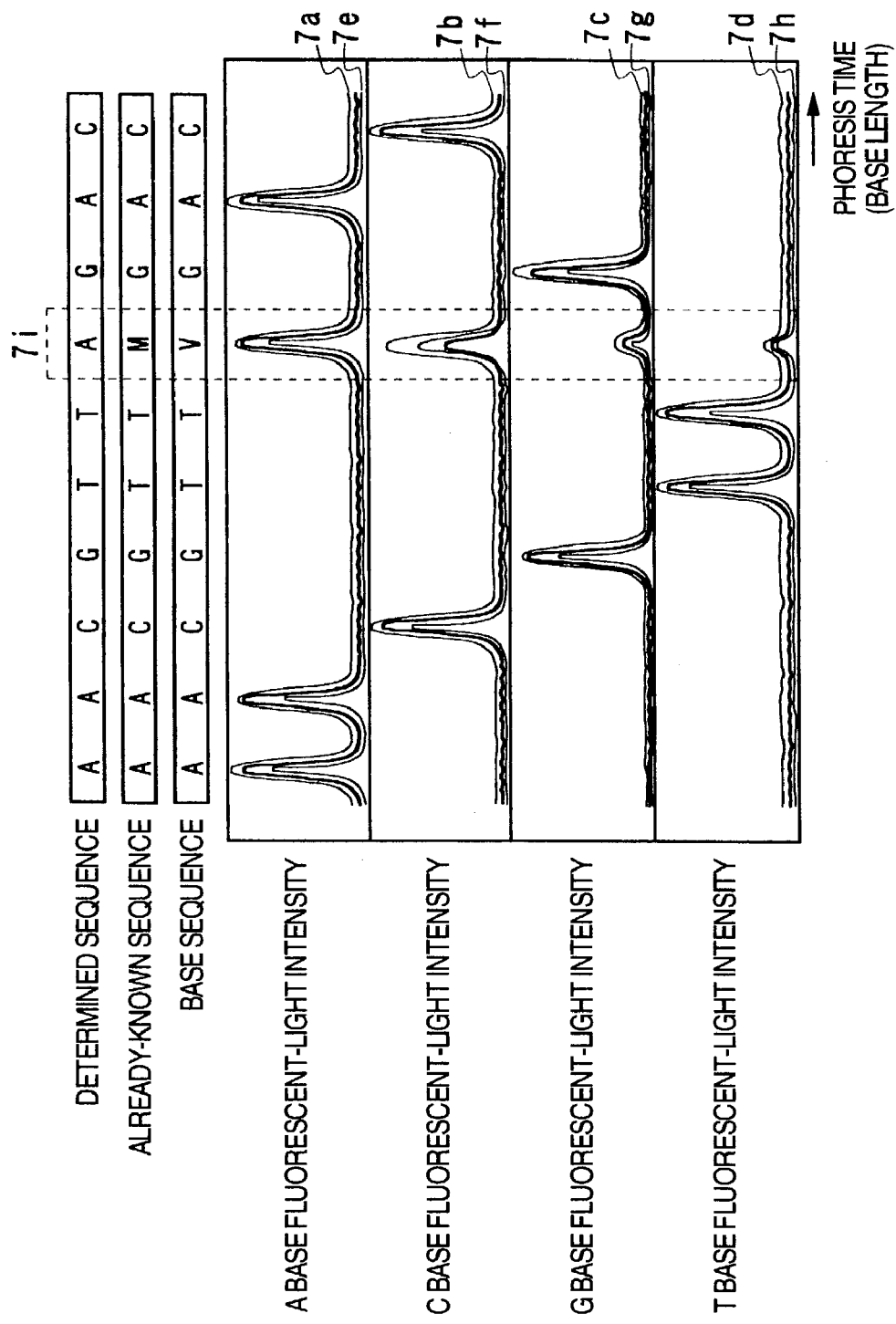
FIG. 7 is an explanatory diagram for explaining the base sequence determination using upper-limit and lower-limit curves according to the present invention.

Also, in the above-described embodiment, although the upper-limit values and the lower-limit values at each peak position have been displayed using the box-and-whisker plots, the upper-limit values and the lower-limit values may also be displayed at all the sampling positions of all the base types as are illustrated in FIG. 7. Here, reference numerals 7a to 7d in the drawing denote the curves indicating the upper-limit values, and 7e to 7h denote the curves indicating the lower-limit values. In this case, with respect to the base types for which there exists none of the identified already-known data, the result may be used which has been obtained by performing the statistical processing to the fluorescent-light intensities of another base type in all the data sets identified as this another base type.

In this embodiment illustrated in FIG. 7, at a peak position 7i, the signal quantity of the fluorescent-light indicating the base type A is positioned between the upper-limit value indicated by 7a and the lower-limit value indicated by 7e, and the signal quantity of the fluorescent-light indicating the base type C is not positioned between the upper-limit value indicated by 7b and the lower-limit value indicated by 7f. This condition allows this unknown base type to be identified as A. Incidentally, here, the already-known sequence (SEQ. ID No. 6) at the peak position 7i indicates M (i.e., the hetero of A and C). This shows that, at this peak position, there exists none of the already-known data identified as the base type G and the base type T. The determined sequence (SEQ. ID No. 5) at the peak position 7i indicates A, and the base sequence (SEQ. ID No. 7) at the peak position 7i indicates V.

Also, in the above-described embodiment, although the explanation has been given concerning the case where the 4 base types of fluorescent-light intensity waveform data are displayed on the 4 graphs independently, the data may also be displayed on 1 graph in a state of being superimposed on each other, using colors or line-types that differ on each base-type basis.

Also, in the above-described embodiment, the explanation has been given regarding the case where the sequence determination is confirmed after displaying the upper-limit value and the lower-limit value in the effective range on the above-described data displaying unit 3d. The signal processing unit 3c, however, may store the determined sequence into the data storing unit 3e after automatically identifying (i.e., automatic determination) the base types positioned within the effective range. Here, the unit 3c performs this automatic determination without performing the display of the upper-limit value and the lower-limit value and the confirmation of the sequence determination as described above.

Also, in the above-described embodiment, the explanation has been given concerning the case of using the statistically-processed result (i.e., already-existing database) of the fluorescent-light intensity waveform data stored in advance into the data storing unit 3e. Furthermore, it is allowable to cause the signal processing unit 3c and the data storing unit 3e to execute the following function: Adding and updating a statistically-processed result, which has been obtained from the newly-measured fluorescent-light waveform data, into the above-described already-existing database automatically or by a manual operation.

Also, in the above-described embodiment, the explanation has been given regarding the case where the upper-limit value and the lower-limit value in the effective range are set up by using the mean value of the already-known data and the standard deviation thereof. Basically the same effect, however, can also be obtained in the case where the maximum value of the already-known data is set up as the upper-limit value and the minimum value thereof is set up as the lower-limit value. Also, basically the same effect can be obtained in the case where the upper-side $\alpha$ (e.g., $\alpha=10$) % percentile of the already-known data (i.e., the point at which, when arranging the data in the order of magnitude, the data is separated in exactly this proportion (i.e., $\alpha$ %) when counted from above) is set up as the upper-limit value, and where the lower-side $\alpha$ % percentile thereof (i.e., the point at which the data is separated in this proportion (i.e., $\alpha$ %) when counted from below) is set up as the lower-limit value. Additionally, when calculating the mean value, the standard deviation, the maximum value, the minimum value, the upper-side $\alpha$ % percentile, and the lower-side $\alpha$ % percentile, the calculations may also be performed after having excluded deviated values (i.e., data positioned at locations far away from the data-value interval where most of the data has been included).

Also, in the above-described embodiment, the explanation has been given concerning the case where the above-described statistical calculation is performed to the above-described corrected result resulting from adding, to the data obtained by the above-described fluorescent-light signal measuring unit 3b, the corrections such as the smoothing correction, the background correction, the smiling correction, the peak-interval correction, and the normalization correction. In addition, the statistical calculation may also be performed to a processed result resulting from omitting some of the above-described correction processings. Otherwise, the statistical calculation may be performed to the very data obtained by the fluorescent-light signal measuring unit 3b.

Incidentally, when performing the statistical calculation with respect to a processed result resulting from omitting the normalization correction (i.e., plural pieces of fluorescent-light intensity waveform data whose base sequences have been already known), it is desirable to perform the following preprocessing in a separate way: "a preprocessing for making the criterions of all the peak intensities identical to each other among all the waveform data (i.e., preprocessing for causing the longitudinal axes to coincide with each other)". The concrete contents of this preprocessing are as follows: At first, the mean peak intensities (i.e., values in the number equivalent to the number of the sequences) at all the peaks are calculated by selecting the respective sequences as the calculation targets. Next, the mean peak intensity (i.e., 1 value) in all the sequences is calculated from these mean peak intensities in the number of the sequences. Moreover, a processing for multiplying each waveform data by a coefficient (=the mean peak intensity in all the sequences/the mean peak intensity in each sequence) is performed so that the mean peak intensity in each waveform data set at all the peaks will become equal to the above-described mean peak intensity in all the sequences. Additionally, instead of using the mean values of the signal intensities at all the peaks, the derivation of the above-described coefficient may be performed as follows: The mean signal intensities at the several peaks (e.g., 20 peaks) existing before and after predetermined peaks and thus including the peaks are calculated sequentially. Then, the coefficient derivation is performed by employing these mean signal intensities as the intensity criterions at the respective predetermined peak positions.

Also, in the above-described embodiment, the explanation has been given regarding the following case: There are prepared the plural pieces of fluorescent-light intensity waveform data measured using the equivalent sequence processings and the equivalent phoresis conditions with respect to the 1 type of nucleic-acid sample on the 1 nucleic-acid base sequence determining apparatus, then storing the statistically-processed result thereto. Meanwhile, plural pieces of fluorescent-light intensity waveform data corresponding to already-known base sequences are prepared on the basis of each different-type nucleic-acid sample, each nucleic-acid base sequence determining apparatus having a different apparatus characteristic, each different sequence processing, and each different phoresis condition, then storing the statistically-processed results thereto based on the respective different situations. This allows the execution of the data interpretation where consideration has been given to variations in the fluorescent-light intensity waveforms that occur by the apparatus dependence, the processing dependence, and the condition dependence.

Figure 8:
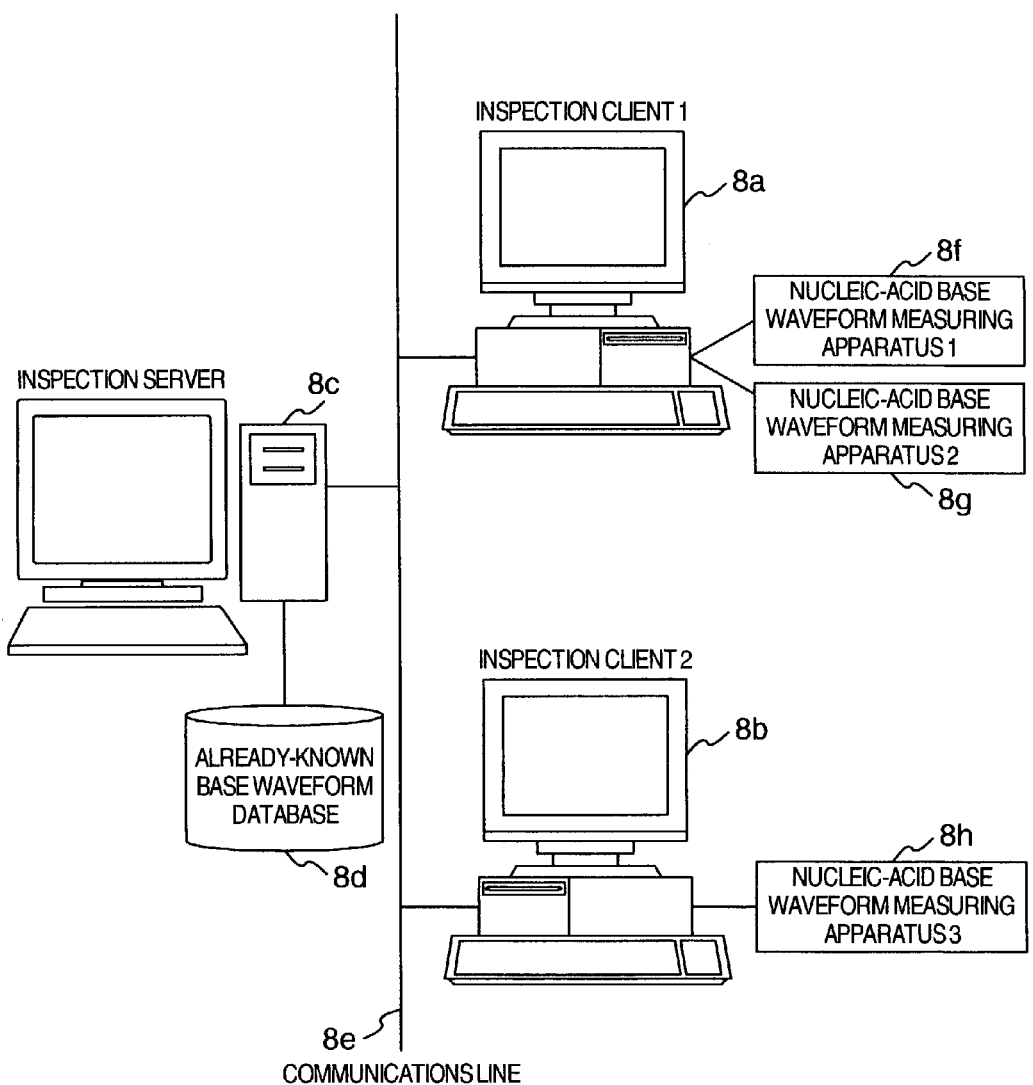
FIG. 8 is a schematic diagram for illustrating the configuration example of a nucleic-acid base sequence inspecting system according to the present invention.
Figure 9:
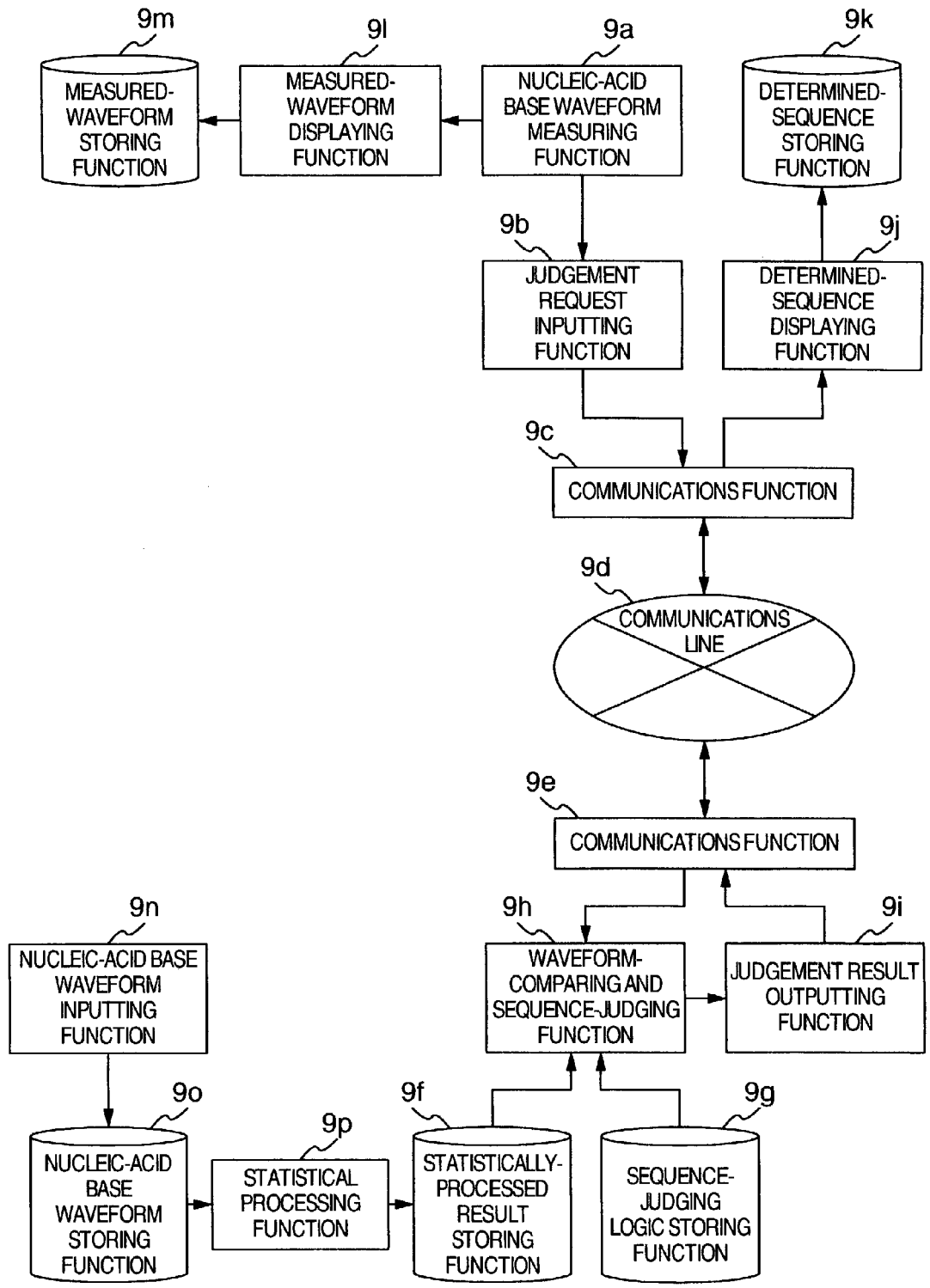
FIG. 9 is a detailed function-block diagram for illustrating the nucleic-acid base sequence inspecting system according to the present invention.

Also, in the above-described embodiment, the explanation has been given concerning the case where the 1 nucleic-acid base sequence determining apparatus includes the following functions: The function for performing the statistical processing of the already-known data and the recording of the processed result, the function for measuring the nucleic-acid fragments so as to acquire the fluorescent-light intensity waveform data, the function for determining the nucleic-acid base sequence by making the comparison between the statistically-processed result and the measured fluorescent-light intensity waveform data, and the like. Meanwhile, as illustrated in FIG. 8, it is also allowable to configure a nucleic-acid base sequence inspecting system including an inspection client 8a (8b) and an inspection server 8c so that distribution of the functions will be implemented in accordance with a detailed function-block diagram illustrated in FIG. 9. Here, the inspection client 8a (8b) includes the function for measuring the nucleic-acid fragments so as to acquire the fluorescent-light intensity waveform data, a communications function, and the like. Also, the inspection server 8c includes the function for performing the statistical processing of the already-known data and the recording (8d) of the processed result, the communications function, the function for determining the nucleic-acid base sequence by making the comparison between the statistically-processed result and the fluorescent-light intensity waveform data acquired by the inspection clients and obtained via a communications line 8e, and the like.

Namely, the following functions allow the inspection client 8a (8b) to request the inspection server 8c to make the sequence judgement on the measured nucleic-acid base waveforms: A function 9a for measuring the nucleic-acid base waveforms, a function 9b for inputting the information (i.e., type of nucleic-acid sample, reaction conditions, phoresis conditions, primer name, data name, and the like) about the base waveform data on which the sequence judgement is requested, a judgement-requested party, and the like, and a function 9c for performing the communications with the inspection server 8c via a communications line 9d (i.e., network).

Also, the following functions allow the inspection server 8c to return the judged base sequence back to the inspection client 8a (8b): A function 9f for storing the information obtained by performing the statistical processing to the plural pieces of fluorescent-light intensity waveform data corresponding to already-known base sequences, a function 9g for storing the judgement conditions at the time of identifying the base sequence, a function 9h for making the comparison between the statistically-processed result and the nucleic-acid base waveforms received via a communications function 9e, and for judging the base sequence in accordance with the judgement conditions, and a function 9i for setting up the judgement-requesting party (i.e., inspection client name, or the like) as the transmission destination, or for setting up the judged base sequence as an output.

Additionally, the inspection client 8a (8b) may also have a function 9j for displaying the returned base sequence, a function 9k for storing the returned base sequence, a function 9l for displaying the measured base waveforms, and a function 9m for storing the measured base waveforms. Also, the inspection server 8c may have a function 9n for inputting the plural pieces of fluorescent-light intensity waveform data corresponding to already-known base sequences, a function 9o for storing the already-known fluorescent-light intensity waveform data, and a function 9p for performing the statistical processing to the plural pieces of fluorescent-light intensity waveform data corresponding to already-known base sequences.

Incidentally, the configuration illustrated in FIG. 8 is one configuration example, and accordingly the application of the present invention is not limited to this configuration. For example, there also may exist a plurality of inspection servers, 3 or more inspection clients, and 4 or more nucleic-acid base sequence determining apparatuses.

Also, in the above-described embodiment, although the explanation has been given concerning the case where the information is transmitted using the communications line, the information may also be transmitted using a storage medium such as a floppy disk or an optical disk.

According to the present invention, when determining the base sequence of A, C, G, and T (or U) by interpreting the fluorescent-light intensity waveform data obtained by measuring the nucleic-acid fragments, the data interpretation is performed by making reference to the information obtained by performing the statistical processing to the plural pieces of fluorescent-light intensity waveform data corresponding to already-known base sequences. This makes it possible to enhance the determination accuracy of the base sequence.

The gene diagnosis (i.e., the DNA marker method) where the 1-base mutation pairs (i.e., the SNPs) or the like are employed as the marker is performed using the apparatus according to the present invention. This permits the judgement accuracy to be enhanced in the search-for of disease genes, the judgement on disease sensitivities, the development of proper medicines (i.e., the tailor-made therapy), and the like.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A computer-implemented nucleic-acid base sequence analyzing method, comprising the steps of:

retrieving by a suitably programmed computer a plurality of fluorescent-light intensity waveform data sets obtained from a nucleic acid sequence, said waveform data sets corresponding to known base sequences;

for each of said plurality of fluorescent-light intensity waveform data sets, performing by the computer normalization processing on fluorescent-light intensities of base types at each of peak positions of the data set with a fluorescent-light intensity of one base type that is maximum fluorescent-light intensity at said each peak position;

calculating by the computer a plurality of mean values (M) and a plurality of standard deviations (S) of fluorescent-light intensity values at said each peak position corresponding to each known base type at said each peak position after said normalization processing;

storing the calculation result obtained by said calculating step in a data storing unit, said storing step including recording the mean values (M) and the standard deviations (S) of the fluorescent-light intensity values at said each peak position corresponding to each known base of said waveform data sets;

retrieving by the computer fluorescent-light intensity waveform data of a nucleic acid fragment of interest from an electrophoresis apparatus which performs electrophoresis on the nucleic acid fragment of interest;

determining by the computer a temporary base sequence of said fragment of interest by calculating ratios between a fluorescent-light intensity of one of four base types which has a maximum intensity value among the four base types and fluorescent-light intensities of the other base types at each peak position, and comparing the calculated respective ratio with predetermined criterion;

retrieving by the computer a base sequence having known bases and homology to the temporary base sequence from the data storing unit by comparing bases of the temporary base sequence with bases of sequences known stored in the data storing unit;

calculating by the computer upper-limit values and lower-limit values based upon the mean values (M) and the standard deviations (S) of each peak position of a known base of the retrieved base sequence which corresponds to said unknown base of the temporary base sequence;

comparing by the computer at each peak position and for each of four base types, each fluorescent-light intensity of four base types of the fragment of interest having the temporary base sequence with the upper-limit value and the lower-limit value respectively corresponding to the known base of the retrieved base sequence, if the fluorescent-light signal intensity of a certain base type at a certain peak position of the fragment of interest is positioned between the upper-limit value and the lower-limit value, identifying that said certain base type is contained at the certain peak position, and if the intensity of the certain base is not positioned between the upper-limit value and the lower-limit value, identifying that said certain base type is not contained at the certain peak position, and identifying a base type at the peak position by combining the base types contained at the peak position, and determining by the computer the nucleic-acid base sequence based on the identified base type at each peak position.

2. The computer-implemented nucleic-acid base sequence analyzing method as claimed in claim 1, wherein said upper-limit value is a summation of the means value (M) and a 3-fold value of the standard deviation (S), and said lower-limit value is a difference between the mean value (M) and the a 3-fold value of the standard deviation (S).

3. The computer-implemented nucleic-acid base sequence analyzing method as claimed in claim 1, wherein the step of performing normalization processing involves normalizing fluorescent-light intensities A0 (n), C0 (n), G0 (n), and T0 (n) of base types A, C, G, T at "n" number of peak positions of the data set, with a maximum fluorescent-light intensity max{A0 (n),C0 (n),G0 (n),T0 (n)} at said each peak position according to equations (1)-(4):

$$A(n)=A_0(n)/\max\{A_0(n),C_0(n),G_0(n),T_0(n)\} \qquad (1)$$

$$C(n)=C_0(n)/\max\{A_0(n),C_0(n),G_0(n),T_0(n)\} \qquad (2)$$

$$G(n)=G_0(n)/\max\{A_0(n),C_0(n),G_0(n),T_0(n)\} \qquad (3)$$

$$T(n)=T_0(n)/\max\{A_0(n),C_0(n),G_0(n),T_0(n)\} \qquad (4).$$

4. The computer-implemented nucleic-acid base sequence analyzing method as claimed in claim 1, wherein the step of calculating a plurality of mean values (M) and a plurality of standard deviations (S) involves calculating with fluorescent-light intensity values $X1(n), X2(n), \ldots, Xm(n)$ at the nth peak position of "m" number of samples for each known base type X=A, C, G, or T at said each peak position according to equations (5)-(6):

$$MX(n) = \sum_{i=1} Xi(n)/m \quad (5)$$

$$SX(n) = \sqrt{\sum \{Xi(n)\}^2/m - \left\{\sum Xi(n)/m\right\}}. \quad (6)$$

5. The computer-implemented nucleic-acid base sequence analyzing method as claimed in claim 1, wherein the step of determining the temporary base sequence involves determining per base type whether a fluorescent-light intensity at one peak position of the fragment of interest falls within a upper-limit value and a lower-limit value corresponding to said each peak position of the retrieved base sequence.

6. The computer-implemented nucleic-acid base sequence analyzing method as claimed in claim 1, wherein the step of determining the temporary base sequence involves comparing the fluorescent-light intensities at said each peak position of said fragment of interest based upon identification criteria: at a peak position, (1) if a second largest fluorescent-light intensity of a second base type is less than a threshold value percentage of a largest fluorescent-light intensity of a first base type, the first base type is identified as the base type of the peak position; and (2) if the fluorescent-light intensity of the second base type is larger than the threshold value percentage of the fluorescent-light intensity of the first base type, and if a third largest fluorescent-light intensity of a third base type is less than the threshold value percentage of the fluorescent-light intensity of the second base type, the first base type is identified as a hetero of the first and second base types at the peak position.

7. The computer-implemented nucleic-acid base sequence analyzing method as claimed in claim 1, wherein the step of retrieving the base sequence, which has known bases and is homologous to the temporary base sequence, involves utilizing a homology-analyzing algorithm.

8. The computer-implemented nucleic-acid base sequence analyzing method as claimed in claim 1, wherein the base sequence, which has known bases and is homologous to the temporary base sequence, is different from the temporary base sequence by only one base.

* * * * *

UNITED STATES PATENT AND TRADEMARK OFFICE
CERTIFICATE OF CORRECTION

PATENT NO. : 7,660,676 B2 Page 1 of 1
APPLICATION NO. : 10/315143
DATED : February 9, 2010
INVENTOR(S) : Hirata et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 469 days.

Signed and Sealed this

Thirtieth Day of November, 2010

David J. Kappos
*Director of the United States Patent and Trademark Office*